United States Patent
LeVey et al.

(10) Patent No.: US 11,067,113 B2
(45) Date of Patent: Jul. 20, 2021

(54) SCREW INSERT AND TOOL FOR USE WITH SCREW INSERT

(71) Applicant: Cerro Wire LLC, Hartselle, AL (US)

(72) Inventors: Kenneth LeVey, Chicago, IL (US);
Randal Hunter, Las Vegas, NV (US);
Christel Hunter, Las Vegas, NV (US)

(73) Assignee: Cerro Wire LLC, Hartselle, AL (US)

( * ) Notice: Subject to any disclaimer, the term of this patent is extended or adjusted under 35 U.S.C. 154(b) by 295 days.

(21) Appl. No.: 16/188,697

(22) Filed: Nov. 13, 2018

(65) Prior Publication Data

US 2019/0078604 A1 Mar. 14, 2019

Related U.S. Application Data

(63) Continuation-in-part of application No. 15/933,728, filed on Mar. 23, 2018, now abandoned.

(60) Provisional application No. 62/477,814, filed on Mar. 28, 2017, provisional application No. 62/579,381, filed on Oct. 31, 2017.

(51) Int. Cl.
| | |
|---|---|
| *F16B 31/02* | (2006.01) |
| *F16B 35/00* | (2006.01) |
| *F16B 37/12* | (2006.01) |
| *F16B 2/06* | (2006.01) |
| *H01R 4/36* | (2006.01) |
| *H01R 43/22* | (2006.01) |

(52) U.S. Cl.
CPC .......... *F16B 31/021* (2013.01); *F16B 35/005* (2013.01); *F16B 37/122* (2013.01); *F16B 2/065* (2013.01); *H01R 4/36* (2013.01); *H01R 43/22* (2013.01)

(58) Field of Classification Search
CPC .. F16B 37/0864; F16B 37/122; F16B 37/125; F16B 31/021; F16B 35/005; F16B 2/065; H01R 4/36; H01R 43/22
See application file for complete search history.

(56) References Cited

U.S. PATENT DOCUMENTS

| | | | |
|---|---|---|---|
| 3,331,267 A * | 7/1967 | Tietge | B25B 23/1415 81/471 |
| 4,838,264 A * | 6/1989 | Bremer | A61B 6/12 411/2 |
| 5,176,050 A * | 1/1993 | Sauer | B25B 23/1415 81/180.1 |

(Continued)

FOREIGN PATENT DOCUMENTS

| | | |
|---|---|---|
| GB | 2517910 A | 3/2015 |
| WO | 0046878 A1 | 8/2000 |

OTHER PUBLICATIONS

International Search Report and Written Opinion issued by ISA/EPO in connection with PCT/US2019/060206 dated Apr. 14, 2020.

(Continued)

*Primary Examiner* — David B. Thomas
(74) *Attorney, Agent, or Firm* — Levenfeld Pearlstein, LLC

(57) ABSTRACT

A screw insert has a body configured to engage a threaded fastener and transmit a torque to the threaded fastener, a separable head connected to the body and a neck extending between body and the separable head. The neck is configured to break causing the separable head to separate from the body in response to a torque applied to the separable head exceeding a predetermined value.

5 Claims, 7 Drawing Sheets

(56) References Cited

U.S. PATENT DOCUMENTS

| | | | | |
|---|---|---|---|---|
| 5,295,831 | A * | 3/1994 | Patterson | A61C 8/0089 |
| | | | | 433/141 |
| 5,299,474 | A * | 4/1994 | Hohmann | B25B 23/1415 |
| | | | | 81/467 |
| 5,347,894 | A * | 9/1994 | Fischer | A61B 17/6433 |
| | | | | 606/104 |
| 6,308,598 | B1 * | 10/2001 | O'Neil | A61B 17/8875 |
| | | | | 81/467 |
| 6,332,382 | B1 * | 12/2001 | Anderson | B25B 15/001 |
| | | | | 81/125 |
| 7,188,556 | B1 * | 3/2007 | Rinner | B25B 15/02 |
| | | | | 81/467 |
| 9,044,286 | B2 * | 6/2015 | O'Neil | B25B 23/1427 |
| 2004/0231467 | A1 | 11/2004 | Hufnagl et al. | |
| 2011/0030516 | A1 * | 2/2011 | Hodges, Jr. | B25B 15/001 |
| | | | | 81/180.1 |
| 2014/0026719 | A1 | 1/2014 | Stanfield et al. | |

OTHER PUBLICATIONS

International Preliminary Report on Patentability issued by ISA/EPO in connection with PCT/US2018/027964 dated Oct. 20, 2020.

* cited by examiner

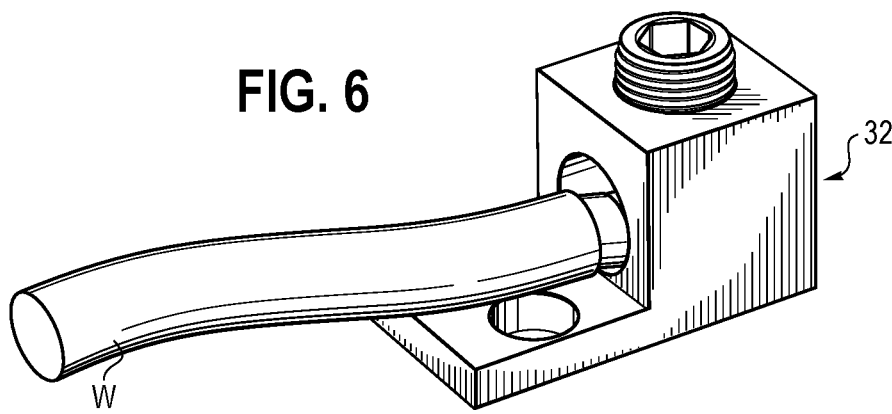
FIG. 6
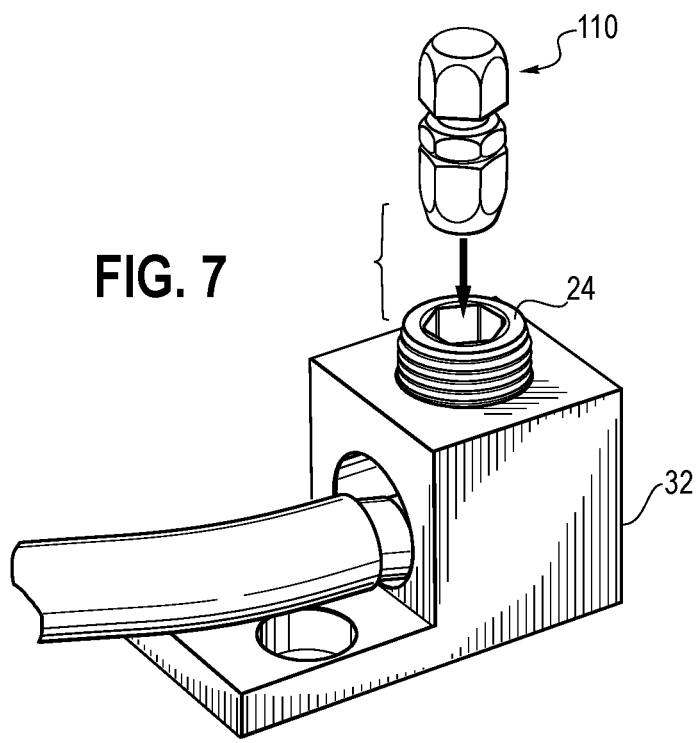
FIG. 7
FIG. 8
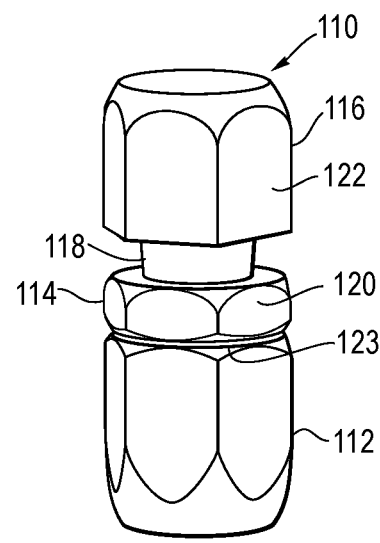

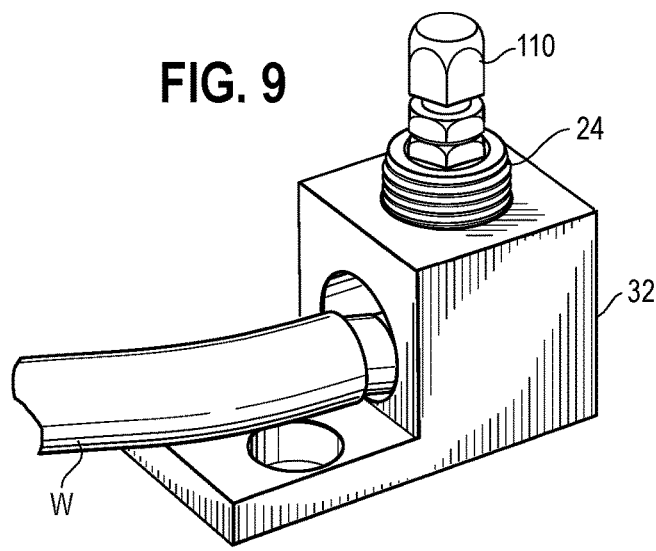
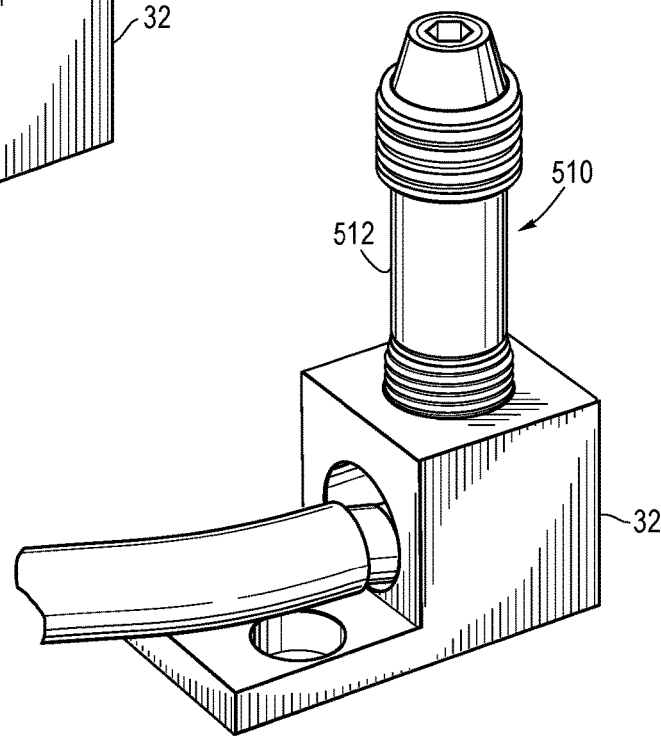
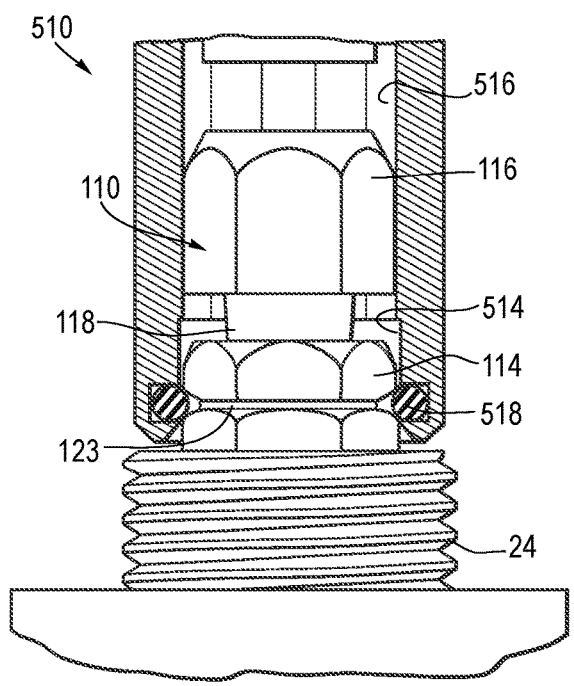

SCREW INSERT AND TOOL FOR USE WITH SCREW INSERT

CROSS-REFERENCE TO RELATED APPLICATION DATA

This application is a continuation-in-part of U.S. patent application Ser. No. 15/933,728, filed Mar. 23, 2018, titled Screw Insert and Tool For Use With Screw Insert, which claims the benefit of and priority to Provisional U.S. Patent Application Ser. No. 62/477,814, filed Mar. 28, 2017, titled Screw Insert, and Provisional U.S. Patent Application Ser. No. 62/579,381, filed Oct. 31, 2017, titled Screw Insert and Tool For Use With Screw Insert, the disclosures of which are incorporated herein in their entireties.

BACKGROUND

The present disclosure relates generally to a screw insert and a tool, and in particular, to a screw insert for controlling torque application to a threaded fastener and a tool for use with the screw insert.

Electrical connectors, and in particular, known connecting lugs for electrical wires, include a housing configured to receive an electrical wire and a set screw to secure the wire in the housing. Typically, the housing is formed as an opening through a lug section of the connector. A threaded bore extends from the opening to an exterior of the lug section in a radial direction. A set screw is threaded in the bore and may be rotated to apply a clamping force to the wire to hold the wire within the opening.

A common set screw is a threaded plug having a hexagonal socket in which a tool may be inserted to apply a torque to the plug. Tightening of the set screw against the wire may be accomplished by applying torque to the set screw using the tool in the manner described above. Currently, the amount of torque applied to the set screw, and consequently, the amount of force applied to the wire by the set screw, is controlled by hand, and is subjective to the worker installing the set screw. Accordingly, set screws may be installed in the connectors with varying level of torque applied to the set screw, and in turn, varying levels of force applied to the wire by the set screw.

Over-torqueing the set screw may result in excess force applied to the wire by the set screw, which may damage the wire. Conversely, under-torqueing of the set screw may result in a loose or otherwise insufficient connection between the connector and the wire. In an effort to address these drawbacks, professional or standard setting organizations are developing new codes requiring all set screw connections to be installed at a predetermined torque. Because current set screw connections are typically installed by "feel," workers may find it difficult to comply with a standard that requires a specific level of torque. One solution may be to equip the tools used for set screw installation with torque gauges, or alternatively, to use a specialized torque wrench. However, such solutions require additional components, new or specialized tools, and may be inconvenient to workers or expensive.

Accordingly, it is desirable to provide a threaded fastener or threaded fastener insert that allows a fastener to be installed to a predetermined torque without the use of additional or specialized tools. A tool for use with the screw insert is also desirable.

SUMMARY

According to one aspect, a screw insert includes a body configured to engage a threaded fastener and transmit a torque to the threaded fastener, a first head connected to the body, a second head connected to the first head and a neck extending between the first head and the second head. The neck is configured to break causing the second head to separate from the first head in response to a torque applied to the second head exceeding a predetermined value.

The body of the screw insert may be substantially polygonal in shape. In one embodiment the body may be substantially hexagonal in shape. The body is configured to engage an internal bore of the threaded fastener.

The first head may include includes one or more first tool engagement sections. The one or more first tool engagement sections may include a plurality of flats disposed along a periphery of the first head. Similarly, the second head may include one or more second tool engagement sections. The one or more second tool engagement sections may be a plurality of flats disposed along a periphery of the second head.

The neck may have a width less than a width of the first head and less than a width of the second head. The neck may include one or more pre-weakened sections configured to separate upon application of a torque exceeding a predetermined torque. In some embodiments, a collar is fitted over the neck.

According to another aspect, a torque limited set screw includes a screw set screw body having screw threads formed on an exterior surface and an internal bore, and a screw insert having body fit into the internal bore. The screw insert also includes a first head disposed at an end of the body, externally of the internal bore, a second head connected to the first head, and a neck extending between the first head and the second head. The neck is configured to break causing the second head to separate from the first head in response to a torque applied to the second head exceeding a predetermined value.

According to another aspect, an electrical connector includes a lug having an axial bore configured to receive a wire, and one or more threaded bores extending through the lug between the axial bore and an exterior of the lug. A set screw body has screw threads formed on an exterior surface and an internal bore and is threadably engaged in one of the threaded bores. A screw insert includes body fit into the internal bore, a first head disposed at an end of the body, externally of the internal bore, a second head connected to the first head, and a neck extending between the first head and the second head. The neck is configured to break causing the second head to separate from the first head in response to a torque applied to the second head exceeding a predetermined value.

According to still another aspect, a screw insert includes a body configured to engage a threaded fastener and transmit a torque to the threaded fastener, a separable head connected to the body, and a neck extending between body and the separable head. The neck is configured to break causing the separable head to separate from the body in response to a torque applied to the separable head exceeding a predetermined value.

The body is configured to be fit in an internal bore of the threaded fastener, and includes a portion extending outwardly from the internal bore. In addition, the body may include a plurality of flats extending along its periphery. The body may have a continuous shape and width along its length.

In an embodiment, the a screw insert includes a body configured to engage a threaded fastener and transmit a torque to the threaded fastener, a first head connected to the body, a second head connected to the first head and a neck extending between the first head and the second head. The neck has a width less than a width of the first head and the second head.

A retaining region is formed in the body outwardly of the neck relative to the first head. The retaining region has a width greater than the neck and less than the first head, and upon application of a torque to the second head exceeding a predetermined torque the neck is configured to break causing the second head to separate from the first head.

The body is substantially hexagonal in shape and the body is configured to engage an internal bore of the threaded fastener. The second head includes one or more second head tool engagement sections. The one or more second tool engagement sections can be a plurality of flats disposed along a periphery of the second head, for example, a hexagonal shape.

The neck can be formed as an undercut having a width. The retaining region can also be formed as an undercut having a width greater than the width of the neck, such that the first and second heads separate at the neck rather than at the retaining region.

A tool is configured for use with a screw insert having a body configured to engage a threaded fastener and transmit a torque to the threaded fastener, a first head connected to the body, a second head connected to the first head, a neck extending between the first head and the second head, wherein the neck has a width less than a width of the first head and the second head and a retaining region formed in the body outwardly of the neck relative to the first head, the retaining region having a width greater than the neck and less than the first head, wherein upon application of a torque to the second head exceeding a predetermined torque the neck is configured to break causing the second head to separate from the first head.

The tool has a body having a having first and second bores and a retaining member. The second bore has a width and a shape for cooperating with the screw insert second head. A torque transmission from the tool to the screw insert is through the engagement of the second bore and the screw insert second head.

Upon application of a torque to the second head exceeding a predetermined torque the neck is configured to break causing the second head to separate from the first head and the retaining member and retaining region cooperate to temporarily hold the screw insert in the tool.

In an embodiment, the retaining region is an undercut and the retaining member is a spring. The tool can include a plunger configured to reciprocate in the body to eject the screw insert from the tool. The plunger can be configured to eject the screw insert from the tool following separation of the second head from the body.

According to another aspect, a screw insert includes a body configured to engage a threaded fastener and transmit a torque to the threaded fastener, a separable head connected to the body and a neck extending between body and the separable head. The neck is configured to break causing the separable head to separate from the body in response to a torque applied to the separable head exceeding a predetermined value. In an embodiment, the head is larger than the body.

In an embodiment, the neck has a cross-sectional dimension that is smaller than a cross-sectional dimension of the body and a cross-sectional dimension of the head. The body and the head can each include a plurality of flats extending along their peripheries. The neck can have a taper that tapers inwardly from the head to the body. In some embodiments, the head and the body have hexagonal cross-sectional shapes and the neck has a circular cross-sectional shape.

The taper can be at an angle of about 0 degrees to about 20 degrees, an angle of about 3 degrees to about 10 degrees and an angle of about 5 degrees.

The head and body hexagonal cross-sectional shapes each define a series of points and flats. In an embodiment, a distance across the points of the body is no more than a distance across the flats of the head. The body of the insert, when fully inserted into a set screw and with the head separated from the body, can extends out of the set screw.

These and other features and advantages of the present invention will be apparent from the following detailed description, in conjunction with the appended claims.

BRIEF DESCRIPTION OF THE DRAWINGS

FIG. 6 illustrates a typical connector or lug;

FIG. 7 is a partially exploded view of the lug showing an embodiment of a screw insert of the present disclosure;

FIG. 8 is a perspective view of the screw insert of FIG. 7;

FIG. 9 is a perspective view illustrating the lug and screw insert of FIG. 8 with the screw insert in the set screw of the lug;

FIG. 10 is a perspective view similar to FIG. 9, showing an embodiment of a tool for use with the screw insert;

FIG. 11 is a partial sectional view of the tool positioned on the screw insert;

DETAILED DESCRIPTION

While the present device is susceptible of embodiment in various forms, there is shown in the figures and will hereinafter be described a presently preferred embodiment with the understanding that the present disclosure is to be considered an exemplification of the device and is not intended to be limited to the specific embodiment illustrated.

Figure 1:
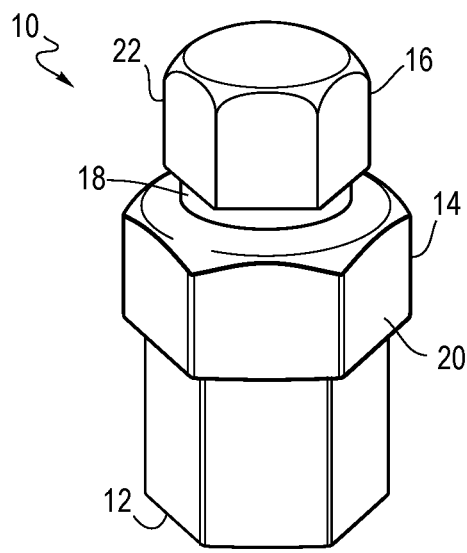
FIG. 1 is a perspective view of a screw insert according to an embodiment described herein.

FIG. 1 is a perspective view of a screw insert 10 according to an embodiment described herein. In one embodiment, the screw insert 10 includes a body 12, a first head 14, a second head 16 and neck 18 interconnected between the first head 14 and the second head 16. In one embodiment, the screw insert 10 is formed as a single, continuous piece and may be made from a suitable material, such as metal, plastic or other suitably rigid material capable of transmitting a desired amount of torque between a tool and a threaded fastener, such as a set screw, as described further below. Suitable metals include, but are not limited to, steel and aluminum.

In one embodiment, the neck 18 is formed as a section of the screw insert 10 having a reduced width relative to the first head 14 and the second head 16. For example, in one embodiment, the neck 18 has a diameter that is less than that of the first head 14 and the second head 16. The neck 18 may be formed as an undercut. In addition, the neck 18 may include one or more pre-weakened sections (not shown) configured to cause the neck 18 to break in response to application of a predetermined torque, such that the second head 16 may be separated from the first head 14. In one embodiment, the pre-weakened sections may be, for example, one or more undercuts, notches, cutouts, stress concentrations, and the like.

One of or both the first head 14 and the second head 16 may include a tool engagement section, configured to be engaged by tool for applying a torque to the screw insert 10. In one embodiment, a first tool engagement section 20 of the first head 14 may be a plurality of flats disposed along a periphery of the first head 14. Similarly, a second tool engagement section 22 of the second head 16 may be a plurality of flats disposed along a periphery of the second head 16. However, the present disclosure is not limited to these configurations. For example, in one embodiment, the tool engagement section 22 of the second head 16 may be a socket or bore configured to receive a tool, such as a key wrench, to apply a torque to the screw insert 10.

The body 12 may be substantially polygonal in shape, and in one embodiment, may be hexagonal in shape. The body 12 is configured to be received in a similarly shaped internal bore of the set screw, so as to transmit a torque applied to the screw insert 10, for example, at the second head 16, to the set screw, as described below.

The tool for applying torque to the screw insert 10 may be, for example, a wrench configured to engage the tool engagement section 20, 22 of the first head 14 or second head 16, respectively. Suitable wrenches include, but are not limited to, adjustable and fixed span wrenches, key-type wrenches, box wrenches, socket wrenches and the like. Other similar, suitable torque-applying tools may be used as well.

Figure 2:
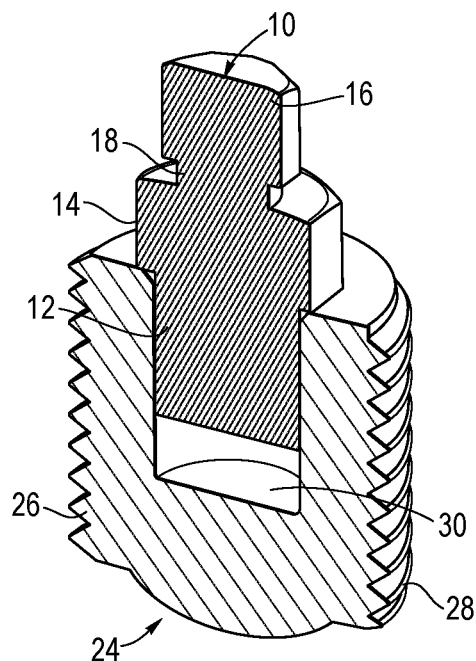
FIG. 2 is a cross-sectional view of the screw insert of FIG. 1 fit into a threaded fastener, according to an embodiment described herein.

FIG. 2 is a cross-sectional view of the screw insert 10 of FIG. 1 disposed in a set screw 24, according to an embodiment described herein. Referring to FIG. 2, in one embodiment, the set screw 24 includes a screw body 26 having screw threads 28 on an exterior surface. The screw body 24 also includes an internal bore 30 configured to receive the screw insert 10.

In one embodiment, the body 12 of the screw insert 10 is at least partially disposed in the internal bore 30. For example, in one embodiment, the screw insert 10 may be press fit within the internal bore 30. Alternatively, or in addition, the body 12 and the internal bore 30 may have substantially the same shape around their respective peripheries, such as a polygonal shape. In one embodiment, the both the body 12 and the internal bore 30 may be hexagonally shaped. Further, in one embodiment, the body 12 may be non-rotatably fit into the internal bore 30. Accordingly, in the embodiments above, a torque applied to the screw insert 10 may be transmitted to the set screw 24 by way of the engagement between the body 12 and the internal bore 30.

Figure 3:
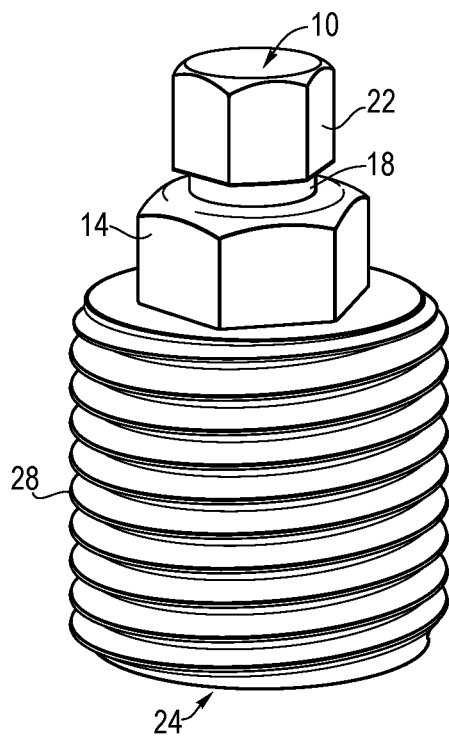
FIG. 3 is a perspective view of the screw insert of FIG. 1, in a first condition, fit into a threaded fastener, according to an embodiment described herein.
Figure 4:
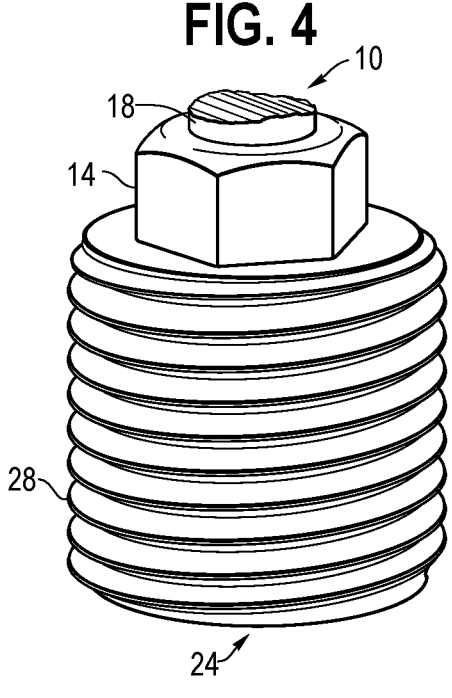
FIG. 4 is a perspective view of the screw insert of FIG. 1, in a second condition, fit into a threaded fastener, according to an embodiment described herein.

FIG. 3 is a perspective view showing the screw insert 10 together with the set screw 24, in a first condition, according to an embodiment described herein. FIG. 4 is a perspective view showing the screw insert 10 together with the set screw 24, in a second condition, according to an embodiment described herein. Referring to FIG. 3, in the first condition, the first head 14, neck 18 and second head 16 extend outwardly from the set screw 24. A tool (not shown) may engage the tool engagement section 22 of the second head 16 to apply a torque to the screw insert 10 in a first direction. The first direction may be, for example, a fastening direction.

As the set screw 24 is fastened (i.e., rotated in the first, fastening direction), the torque required to continue rotating the set screw 24 in the first direction increases. Upon application of a predetermined torque to the screw insert 10, the neck 18 breaks and the second head 16 separates from the first head 14 as shown in FIG. 4. Thus, in the second condition, the second head 16 is separated from the first head 14. Accordingly, a torque transmitted to the set screw 24 by way of a torque applied to the second head 16, is limited by torque that may be transmitted through the neck 18 before breaking.

The tool may apply a torque to the first head 14 in a second direction, opposite to the first direction. The second direction may be, for example, a removal direction. Through application of a torque in the second direction to the first head 14, the set screw 24 may be caused to rotate in the second direction to remove the set screw 24 or reduce a clamping force applied by the set screw 24 as described below.

Figure 5:
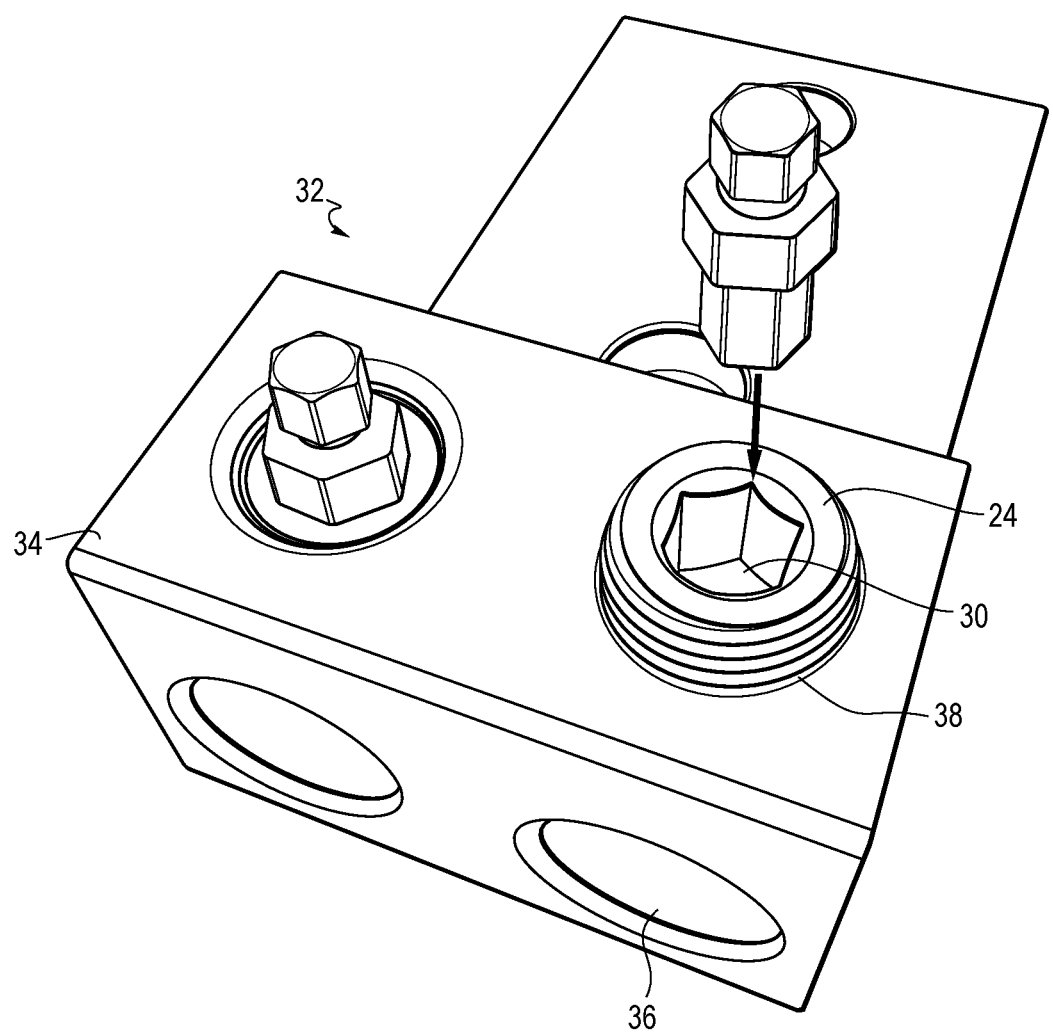
FIG. 5 is a perspective view showing an example of a connector for use with the screw insert and screw of FIGS. 2-4, according to an embodiment described herein.
Figure 12:
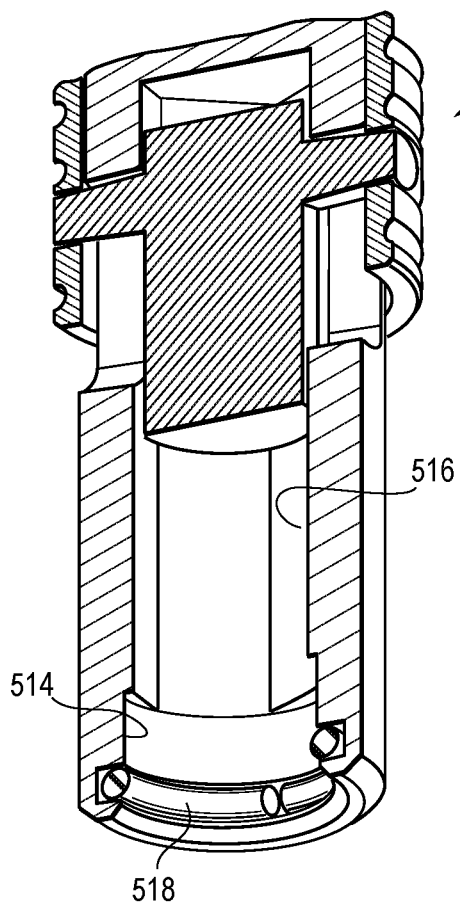
FIG. 12 is a partial sectional view of the tool of FIGS. 10 and 11.

FIG. 5 is a perspective view showing an example of an electrical connector 32 with which the set screw 24 and screw insert 10 described in the embodiments above may be used. In one embodiment, the electrical connector 32 may include a lug 34 having one or more axial bores 36 and one or more internally threaded bores 38 configured to receive the set screw 24. Rotation of the set screw 24 in the first, or fastening direction, through threaded engagement between the internally threaded bores 38 and the set screw 24, causes the set screw 24 to move toward and/or into the axial bore 36 to apply the clamping force to a wire or other object positioned in the axial bore 36. Rotation of the set screw 24 in the second, or removal direction, through threaded engagement between the internally threaded bore 38 and the set screw 24, causes the set screw 24 to move away from the axial bore 36, to reduce a clamping force applied to the wire or other object, and/or to remove the set screw 24 from the internally threaded bore.

In use, according to one embodiment, the screw insert 10, for example, the body 12 may be engaged with the set screw 24 in such a manner that a torque applied to the screw insert 10 is transmitted to the set screw 24 to cause the set screw 24 to rotate within a threaded bore 38 of electrical connector 32. The torque may be applied to the screw insert 10 with a tool at the tool engagement section 22 of the second head 16. As the set screw 24 bears against a wire or other object to be fastened within the axial bore 36 of the electrical connector 32, a larger torque is required to continue rotating the set screw 24. Upon application of a predetermined level of torque to the second head 16, the neck 18 breaks, thereby separating the second head 16 from the first head 14, and consequently, limiting the torque applied to the set screw 24. In turn, a clamping force applied by the set screw 24 (due to rotation of the set screw in the threaded bore) to the wire or other object is limited as well. After the second head 16 is separated from the first head 14, the tool may engage the tool engagement section 20 of the first head 14 to apply a torque in an opposite direction, which is transmitted to the set screw 24 to rotate the set screw 24 in an opposite direction for removal from the threaded bore 38 or to reduce a clamping force on the wire or other object in the axial bore 36.

According to another embodiment, the body 12 and the first head 14 may be formed having a substantially continuous width and shape as one another. Or, said differently, the first head 14 may be omitted and the body 12 may extend outwardly from the internal bore 30 of the threaded fastener 24. In such an embodiment, the body 12 has a length greater than a length of the internal bore 30. A separable head, such as the second head 16 described in the embodiments above, may be connected to the body 12 by way of the neck 18. The neck 18 is configured to break upon application of a torque to the separable head 16 that exceeds a predetermined torque. Breaking the neck 18 causes the separable head 16 to separate from the body 12.

The body 12, including the portion extending outwardly from the internal bore 30, may be formed having a plurality of flats extending along its periphery. Thus, the plurality of flats on the portion of body extending outwardly from the internal bore may serve as a tool engagement section, similar to the first tool engagement section 20 described in the embodiments above. Accordingly, after separating the separable head 16 from the body 12, a torque may be applied to the body 12, for example, at the portion extending outwardly from the internal bore, for removal of the threaded fastener.

An alternate embodiment of the set screw is illustrated in FIGS. 7-14B, while FIG. 6 illustrates a standard lug 32. The screw insert 110 includes a body 112, a first head 114, a second head 116 and a neck 118 interconnected between the first head 114 and the second head 116. As with the previous embodiment, the screw insert 110 can be formed as a single, continuous piece and made from a suitable material, such as metal, plastic or other suitably rigid material capable of transmitting a desired amount torque between a tool and a threaded fastener, such as a set screw. Suitable metals include, but are not limited to, steel and aluminum.

In such an embodiment, the neck 118 is formed as a section of the screw insert 110 having a reduced width, e.g., diameter, relative to the first head 114 and the second head 116. For example, the neck 118 may be formed as an undercut. In addition, the neck 118 may include one or more pre-weakened sections (not shown) configured to cause the neck 118 to break in response to application of a predetermined torque, such that the second head 116 separates from the first head 114. In one embodiment, the pre-weakened sections may be, for example, one or more undercuts, notches, cutouts, stress concentrations, and the like in which the neck 118 has a smaller width or diameter than the first and/or second heads 114, 116.

The first head 114 and the second head 16 may each include a tool engagement section, 120, 122, respectively. One or both of the tool engagement sections 120, 122 can be configured to be engaged by tool for applying a torque to the screw insert 110. In an embodiment, the first and second head tool engagement sections 120, 122 are a plurality of flats disposed along a periphery of the respective heads 114, 116. However, the present disclosure is not limited to these configurations. For example, in an embodiment, the second head tool engagement section 122 may be a socket or bore configured to receive a tool, such as a key wrench, to apply a torque to the screw insert 110.

In an embodiment, a retaining section 123 is disposed between the body 112 and the first head 114. The retaining section 123 can be formed as an undercut, similar to the neck 118, but not as a weakened section as weakened as the neck 118. It will be appreciated that the retaining section or channel 123, being of a lesser width or diameter than the body, 112, first or second heads 114, 116 may be a weaker section than the body 112 and heads 114, 116, but it is not as weakened as the neck 118.

The body 112 may be substantially polygonal in shape, and in embodiments, may be hexagonal in shape such that it is configured to be received in a similarly shaped internal bore of the set screw 24, so as to transmit a torque applied to the screw insert 110, for example, at the second head 116, to the set screw 24.

Figure 15A:
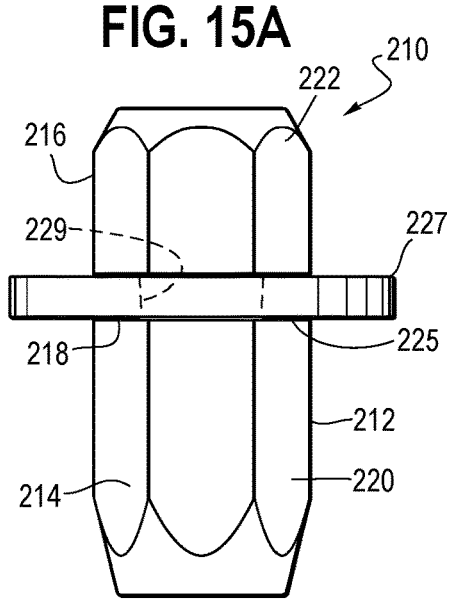
FIGS. 15A and 15B illustrate an embodiment of the screw insert that has a shield or tool stop positioned on the insert.
Figure 15B:
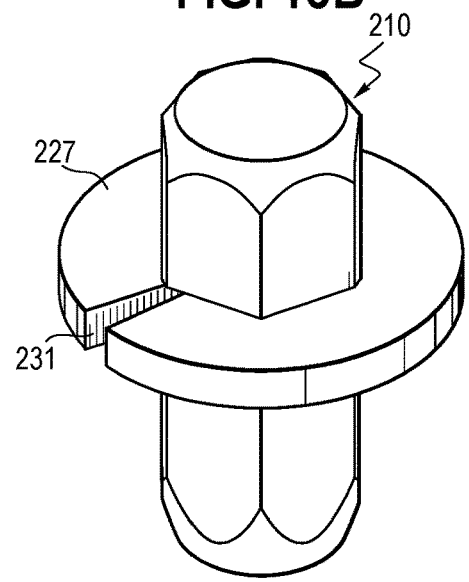

FIGS. 15A and 15B illustrate an embodiment of the screw insert 210 that includes a tool collar or shield 227. In this example, the screw insert includes a body 212 having a first head 214, a second head 216 and a neck 218 interconnected between the body 212/first head 214 and the second head 216. As with the previous embodiments, the screw insert 210 can be formed as a single, continuous piece and may be made from a suitable material, such as metal, for example, steel or aluminum, plastic or other suitably rigid material capable of transmitting a desired amount of torque between a tool and a threaded fastener, such as a set screw, as described above.

The body 212/first head 214 and the second head 216 may each include a tool engagement section, 220, 222, respectively, which, as with the previous embodiments, can be configured to be engaged by tool for applying a torque to the screw insert 210 and for transferring torque to the set screw 24. In an embodiment, the first and second head tool engagement sections 220, 222 are a plurality of flats disposed along a periphery of the body/first head 214 and the second head 216. However, the present disclosure is not limited to these configurations. For example, and as described above with respect to the previous embodiments, the second head tool engagement section 222 may be a socket or bore configured to receive a tool, such as a key wrench, to apply a torque to the screw insert 210.

In embodiments in which the shape (the hexagonal shape) and size of the body 212/first head 214 and the second head 216 are the same size, the shield 227 can be positioned in the undercut or notch 225 formed by the neck 218. This prevents over insertion of the tool onto the screw insert 210 and over insertion of the screw insert 210 in the set screw 24. As such, the shield 227 positions the screw insert 210 in the set screw 24 and in the tool to ensure that the neck 218 is properly positioned to break upon exceeding the predetermined force or torque.

In an embodiment, the shield 227 is a fairly rigid member, but is sufficiently flexible that it can be positioned on the screw insert 210. In an embodiment, the shield has a central opening 229, preferably about the same diameter as the neck 218, and a slit 231 extending from a periphery of the shield 227 to opening 229 to allow the shield to be positioned on the screw insert 210. For example, the shield 227 can be formed from a polymeric material (a plastic) or fibrous material that permits the shield 227 to be bent or flexed to fit onto the neck 218.

FIGS. 16A-16D illustrate yet another embodiment of the screw insert 310. The screw insert 310 includes a body 312, a head 314, and a neck 318 extending between and connecting the body 312 and the head 314. The head 314 body 312 can be configured having tool engagement sections 320, 322, respectively. In an embodiment, the screw insert 310 is formed as a single, continuous piece and may be made from a suitable material, such as metal, plastic or other suitably rigid material capable of transmitting a desired amount of torque between a tool and a threaded fastener, such as a set screw 24, as described further below. Suitable metals include, but are not limited to, steel and aluminum.

In an embodiment, the neck 318 is formed as a section of the screw insert 310 having a reduced width relative to the head 314 and the body 312. For example, in one embodiment, the neck 318 is round and has a diameter $d_{318}$ that is less than a smallest dimension across the head 314 and the body 312. For example, the head 314 and body 312 may be formed having hexagonal shapes that define points 324, 326 and flats 328, 330 and dimensions $d_{324}$, $d_{326}$, $d_{328}$, $d_{330}$, across the respective points and flats, and the neck 318 has a diameter $d_{318}$ that is less than the smallest dimension $d_{330}$ across the body flats 330 (the dimension across body flats is the smallest of the head 314 and body 312 dimensions). The neck 318 may be formed as an undercut. In addition, the neck 318 may include one or more pre-weakened sections configured to cause the neck 318 to break at a generally predetermined location in response to application of a predetermined torque, such that the head 314 may be separated from the body 312. In an embodiment, the neck 318 may have, for example, a taper indicated at angle α that tapers inwardly from the head 314 to the body 312. In such a tapered configuration, the neck 318 has a smaller diameter at a juncture with the body 312. Such a taper can influence or control a break zone, or where the neck 318 separates from the body 312. Preferably, the neck 318 separates at or near to the juncture with the body 312 so to leave little or none of the neck 318 remaining on the body 312. In a present screw insert, the neck 318 has a taper angle α of about 0 degrees to about 20 degrees, and preferably about 3 degrees to about 10 degrees and preferably about 5 degrees relative to a longitudinal axis $A_{310}$ through the insert 310. Other pre-weakened sections can include one or more undercuts, notches, cutouts, stress concentrations, and the like.

Figure 16A:
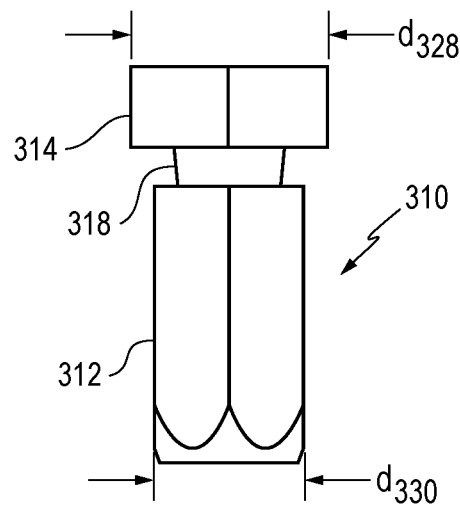
FIGS. 16A-16D illustrate yet another embodiment of the set screw insert.
Figure 16B:
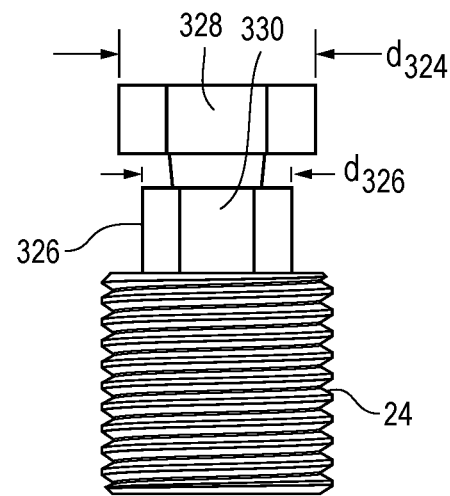
Figure 16C:
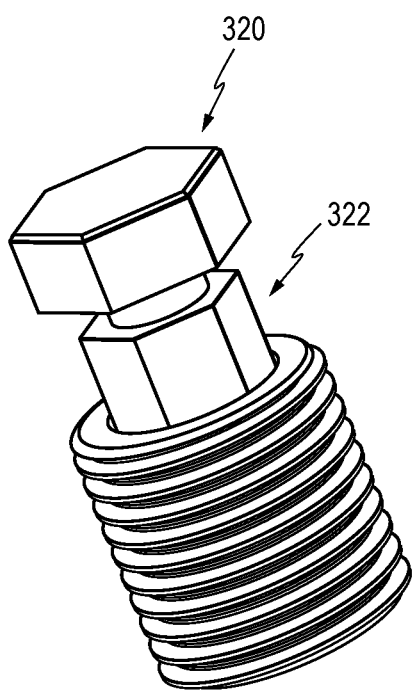
Figure 16D:
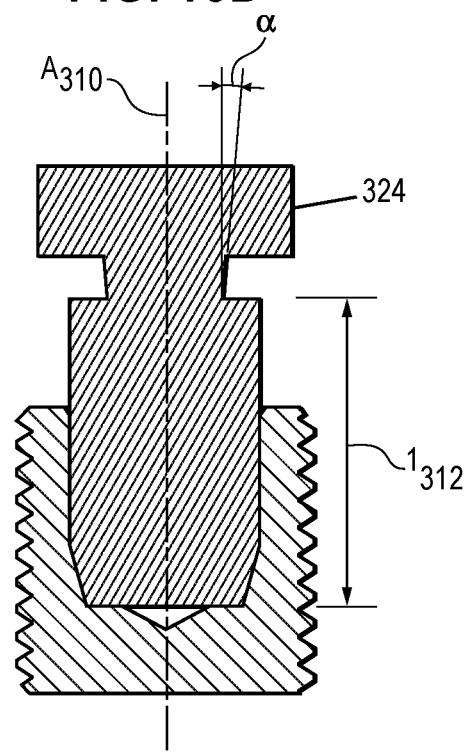

As seen in FIG. 16D, the portion of the insert 310 that remains after the head 314 has been removed (which is the body 312 and may include a small portion of the neck 318), is sufficiently long 1312 and extends out of the set screw 24 a sufficient amount so that a tool, such as a wrench or socket can be applied to it.

In an embodiment in which the head 314 and body 312 have hexagonal shapes, the distance $d_{326}$ across the body points is no greater than, and preferably less than the distance $d_{328}$ across the head flats. In this manner, a wrench or socket sized to fit on the head 314 and positioned on the head 314 (and over an upper portion of the body 312) will not engage body 312 when the neck 318 breaks, but will only engage the head 314. In this manner, when, for example, a socket is positioned on the insert 310 all the way to the top of the set screw 24, once the proper torque is achieved and the head 314 separates from the body 312 (at the neck 318), the tool will not continue to engage and drive the insert 310 in that the tool will not engage the body 312.

FIGS. 10-14B illustrate, at least in part, a tool 510 for use with the screw insert 110. It will be understood from the following description that the tool 510 can be used with the disclosed embodiments of the screw insert 10, 110. The tool 510 includes a body 512 having first and second bores 514, 516, respectively, such as the illustrated coaxial bores, a retaining member 518, such as a retaining ring or retaining spring that cooperates with the retaining channel 123, and a plunger 520. In an embodiment, the second bore 516 has a smaller diameter or width than the first bore 514. The second bore 516 has a shape to cooperate with the second head 116 when driving the screw insert 110 such that the sides of the bore 516 engage the second head tool engagement section 122. In an embodiment, the second head 116 and the second bore 516 both have a hexagonal shape.

The first bore 514 can have any shape, although for purposes of tooling and manufacture, it is anticipated that the first bore 514 may have a shape similar to that of the second bore 516. The first bore 514 is sized so that when the screw insert 110 is positioned in the tool 510, the walls of the first bore 514 do not transmit a torque to the first head 114. That is, torque transmission from the tool 510 to the screw insert 110 is through the engagement of the second bore 516 (the walls that define the bore 516) and the screw insert second head 116.

Figure 14A:
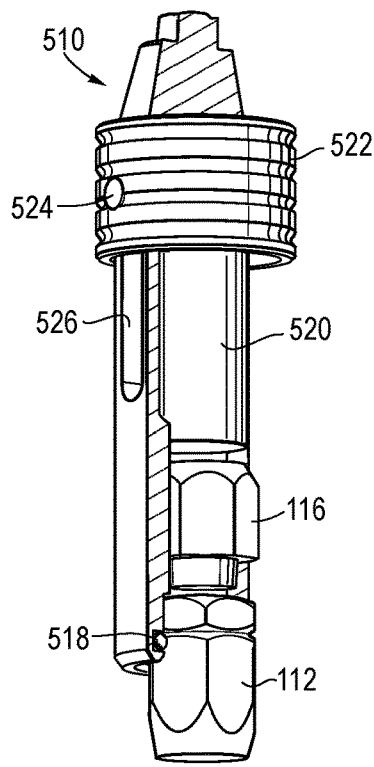
FIGS. 14A and 14B are partial sectional views of the tool with a separated screw insert in the tool (FIG. 14A) and as the separated screw insert is ejected from the tool (FIG. 14B)
Figure 14B:
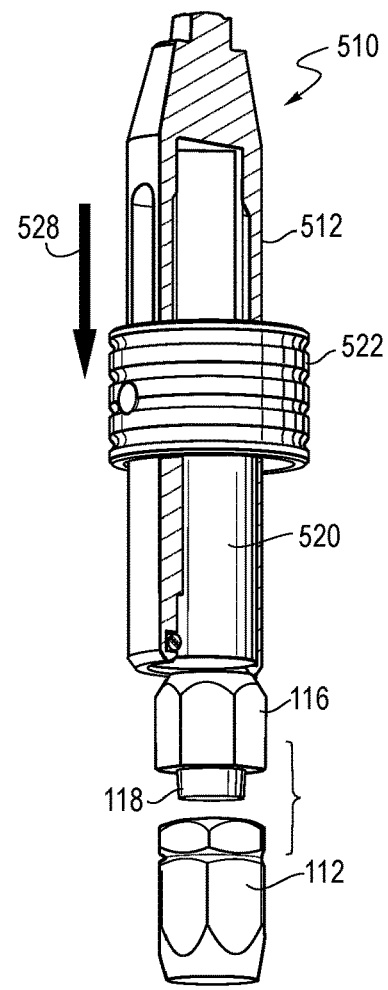

The plunger 520 is positioned in the tool 510 for reciprocating movement within the second and first bores 516, 514, respectively. As will be described in more detail below, the plunger 520 is used to eject the portion or portions of the screw insert 110 that remain in the tool 510 following use. In an embodiment the plunger 520 includes an external grasping ring 522 to allow a user to grasp the ring 522 to reciprocate (slide) the plunger 520 between a retracted position (FIG. 14A) and an extended (ejection) position (FIG. 14B). The ring 522 can be operably connected to the plunger 520 by one or more pins 524 that extend through one or more slots 526 in the tool body 512.

FIG. 7 illustrates the screw insert 110 in an exploded view relative to a set screw 24 and connector or lug 32. FIG. 9 shows the screw insert 110 positioned in the set screw 24. The body 112 is positioned in the set screw 24 with the first and second heads 114, 116 outside of the bore in the set screw 24. FIG. 10 illustrates the tool 510 positioned on the screw insert 110, and FIG. 11 is a sectional view of the tool 510 as it is positioned on the screw insert 110 in the set screw 24. As can be seen from FIG. 11, the plunger 520 is in the retracted position and the tool retaining spring 518 is positioned in the screw insert retaining channel 123. The engagement of the tool retaining spring 518 and the screw insert retaining channel 123 permits the screw insert 110 to be temporarily retained in the tool 510 during driving.

Torque is transmitted from the tool 510 to the screw insert 110. Because the first head 114 is smaller than the first bore 514, the torque is transmitted to the screw insert 110 (and set screw 24) only from the second bore 516 through the screw insert second head 116. When a predetermined torque is reached, that is as the set screw 24 bears against a wire W or other object to be fastened within the lug or connector 32, continued driving (rotation) of the screw insert 110 and set screw 24 results in a torque greater than the predetermined torque. As a result, the neck 118 breaks, separating the second head 116 from the first head 114. It will be understood that breaking the neck 118 limits the torque applied to the set screw 24.

Figure 13:
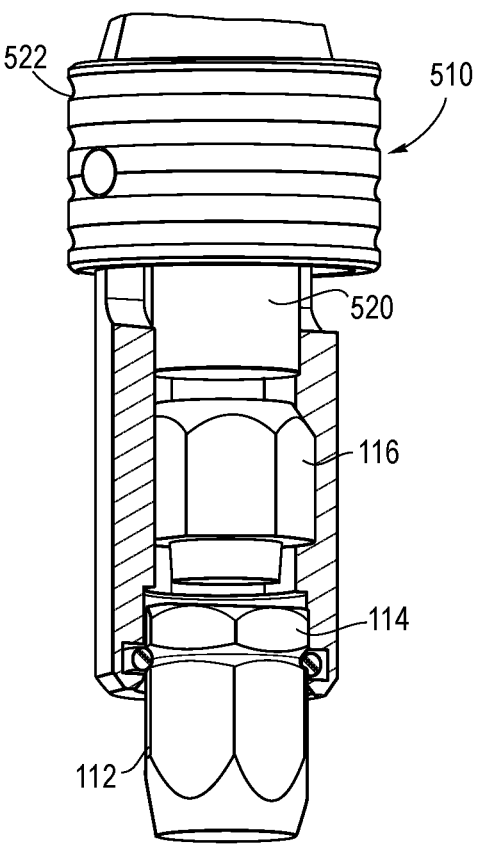
FIG. 13 is a partial sectional view of the tool and a separated screw insert in the tool, for example, following use and prior to ejection of the screw insert from the tool.

It will also be appreciated that the entirety of the screw insert 110 is a consumable. That is, it is a single use element that it is disposed of after use. As noted above, the engagement of the tool retaining spring 518 cooperates with the screw insert retaining channel 123 to temporarily secure the screw insert 110 in the tool 510 to hold the screw insert 510 in the tool 510 before use, and after use (after the neck 118 breaks and the second head 116 is separated from the first head 114 and body 112). This permits readily removing the entirety of the screw insert 110 (that is, the second head 116 as separated from the first head 114 and body 112) from the set screw 24, as shown in FIGS. 13 and 14A. The plunger 520 can then be urged downward (as indicated by the arrow at 528), into contact with the second head 116, which pushes the screw insert 110 (the first and second heads 114, 116)

from the tool 510 as seen in FIG. 14B. The plunger 520 can then be returned to the retracted condition for loading a new set screw.

It is understood that the screw insert 10 and screw insert 10 together with the set screw 24 described in the embodiments above are not limited to uses with electrical connectors. Those skilled in the art will recognize that the screw insert 10 may be used with set screws or other threaded fasteners in different applications where it is desirable to control or limit the amount of torque applied and/or a clamping force applied by a set screw.

It is also understood the various features from any of the embodiments above are usable together with the other embodiments described herein. Further, it is understood that same or similar terminology used across the different embodiments above refers to the same or similar component, with the exception of any differences described or shown in the figures.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover all such modifications as fall within the scope of the claims.

What is claimed is:

1. A screw insert comprising:
   a body configured to engage a threaded fastener and transmit a torque to the threaded fastener;
   a separable head connected to the body;
   a neck extending between body and the separable head, wherein the neck breaks causing the separable head to separate from the body in response to a torque applied to the separable head exceeding a predetermined value, wherein the neck has a cross-sectional dimension that is smaller than a smallest cross-sectional dimension of the body and a smallest cross-sectional dimension of the head, the neck having a circular cross-sectional shape tapering inwardly from the head to the body, the taper being formed at an angle of about 3 degrees to about 10 degrees, such that the neck has a smallest diameter at a juncture with the body, and wherein a distance across the points of the body is no more than a distance across the flats of the head.

2. The screw insert of claim 1, wherein the body includes a plurality of flats extending along its periphery and the head has a plurality of flats extending along its periphery.

3. The screw insert of claim 2, wherein the head has a hexagonal cross-sectional shape and the body has a hexagonal cross-sectional shape.

4. The screw insert of claim 1, wherein the taper is at an angle of about 5 degrees.

5. The screw insert of claim 1, wherein when fully inserted into a set screw and with the head separated from the body, the body extends out of the set screw.

* * * * *